US009603678B2

(12) United States Patent
Mourão Martinez et al.

(10) Patent No.: US 9,603,678 B2
(45) Date of Patent: Mar. 28, 2017

(54) SYSTEM OF COMPENSATORY SLANTED COPINGS, CONVERTERS AND EXTENDERS AND ABUTMENTS OF UNIVERSAL COUPLING OVER OSSEOINTEGRATED IMPLANTS

(75) Inventors: Maria Auxiliadora Mourão Martinez, Belo Horizonte (BR); Luciana Silva Colepícolo, Belo Horizonte (BR); Branca Fraga de Resende Chaves, Belo Horizonte (BR)

(73) Assignee: ITP—Instituto de Tecnologia e Pesquisa LTDA, Belo Horizonte (BR)

( * ) Notice: Subject to any disclaimer, the term of this patent is extended or adjusted under 35 U.S.C. 154(b) by 0 days.

(21) Appl. No.: 12/601,659

(22) PCT Filed: Oct. 17, 2007

(86) PCT No.: PCT/BR2007/000276
§ 371 (c)(1),
(2), (4) Date: Dec. 30, 2009

(87) PCT Pub. No.: WO2008/141404
PCT Pub. Date: Nov. 27, 2008

(65) Prior Publication Data
US 2010/0129774 A1   May 27, 2010

(30) Foreign Application Priority Data
May 24, 2007   (BR) ..................... 0705570

(51) Int. Cl.
*A61C 8/00*   (2006.01)
(52) U.S. Cl.
CPC ............ *A61C 8/005* (2013.01); *A61C 8/0034* (2013.01); *A61C 8/0053* (2013.01); *A61C 8/006* (2013.01); *A61C 8/0068* (2013.01); *A61C 8/0071* (2013.01)
(58) Field of Classification Search
CPC ..... A61C 8/0034; A61C 8/005; A61C 8/0053; A61C 13/00; A61C 8/006; A61C 8/0068; A61C 8/0071
(Continued)

(56) References Cited

U.S. PATENT DOCUMENTS

| 4,988,297 A | * | 1/1991 | Lazzara | ............... A61C 8/0001 433/173 |
| 5,000,685 A | * | 3/1991 | Brajnovic | ..................... 433/173 |

(Continued)

FOREIGN PATENT DOCUMENTS

| EP | 0 583 829 | 2/1994 |
| WO | WO 01/52765 | 7/2001 |
| WO | WO 2007/059595 | 5/2007 |

OTHER PUBLICATIONS

International Search Report and Written Opinion from International Patent Application No. PCT/BR2007/000276, filed Oct. 19, 2007.

*Primary Examiner* — Cris L Rodriguez
*Assistant Examiner* — Mirayda A Aponte
(74) *Attorney, Agent, or Firm* — Remenick PLLC

(57) ABSTRACT

The present invention refers to a system of prosthetic components consisting of Compensatory Slanted Copings and Abutments of Universal Coupling that function as a set of coupled parts that allow corrections of slants that vary between OQ and 60Q, of fixing osseointeg rated implants, including zygomatic fixations, and it provides a cap, molding transferer and screws for fastening and locking. This system of copings and abutments provides properties of conversion and extension of the implants. Its shape provides better occlusal stability and favorable biomechanics, since the forces are better distributed, diminishing the concentration of tension on the fitting platform of the implant, as well as the screws. The abutments of the universal coupling can be readjusted and be cemented or screwed. In the present system, the superior platform of the coping and the inferior base of the abutment are universalized, since the inferior platform of the coping corrects the slant of the implant. It has screws for fastening and for locking of the coping/abutment set. The characteristics of this system provide great versatility, which allows it to be used in various areas of medicine.

25 Claims, 1 Drawing Sheet

(58) Field of Classification Search
 USPC .......................... 433/172–176, 201.1, 221.1
 See application file for complete search history.

(56) References Cited

U.S. PATENT DOCUMENTS

| | | | |
|---|---|---|---|
| 5,069,622 | A | 12/1991 | Rangert et al. |
| 5,092,771 | A | 3/1992 | Tatum, III |
| 5,116,225 | A * | 5/1992 | Riera .............................. 433/173 |
| 5,350,301 | A * | 9/1994 | De Buck ........................ 433/173 |
| 5,651,675 | A * | 7/1997 | Singer .................... A61C 8/008 |
| | | | 433/172 |
| 5,863,200 | A * | 1/1999 | Hamada et al. .............. 433/173 |
| 6,848,908 | B2 | 2/2005 | Bjorn et al. |
| 6,994,547 | B1 | 2/2006 | Sethi et al. |
| 7,905,727 | B2 * | 3/2011 | Kikuchi ......................... 433/189 |
| 2003/0031982 | A1 * | 2/2003 | Abarno ................ A61C 8/0022 |
| | | | 433/173 |
| 2004/0029075 | A1 * | 2/2004 | Peltier et al. ................. 433/173 |
| 2005/0266381 | A1 * | 12/2005 | Abarno .................. A61C 1/084 |
| | | | 433/173 |
| 2006/0106484 | A1 * | 5/2006 | Saliger et al. ................. 700/182 |
| 2006/0286509 | A1 * | 12/2006 | Bassett ................ A61C 8/0006 |
| | | | 433/173 |
| 2008/0293012 | A1 | 11/2008 | Chaves et al. |

* cited by examiner

SYSTEM OF COMPENSATORY SLANTED COPINGS, CONVERTERS AND EXTENDERS AND ABUTMENTS OF UNIVERSAL COUPLING OVER OSSEOINTEGRATED IMPLANTS

CROSS REFERENCE TO RELATED APPLICATIONS

This application is a national stage application filed under 35 U.S.C. §371 of International Application No. PCT/BR2007/000276, filed Aug. 17, 2007, which claims priority from Brazilian Application No. PI0705570-6, filed May 24, 2007, each of which is incorporated by reference herein.

The present invention refers to a system of dental prosthetic components, consisting of slanted compensatory copings, converters and extenders, abutments of universal couplings, caps and screws for osseointegrated prosthetic reconstruction, as well as transferers for molding.

BACKGROUND OF THE INVENTION

The use of osseointegrated implants is currently widespread. Today, slanted implants are the most recommended, but the state of the art still does not provide solutions for various problems related to prosthetic reconstruction of implants, mainly with regard to the slanted types, presenting some limitations of a biomechanical nature, which can cause the increase in tension and bone loss due to a lack of more appropriate passive fitting.

The options offered for the problem of the abutment fitting on slanted implants, in the state of the art, are cited in the patents U.S. Pat. No. 6,848,908 and U.S. Pat. No. 5,069,622 that deal with angled abutments. In these cases, these abutments present limitations in the variations of angulations, high manufacturing cost and, consequently, a high final cost for the treatment. In a search carried out on the patents database, BR 0505827-9 and its respective Certificate of Addition have solved the existing problem, in the state of the art, for prosthetic reconstruction on implants. However, this reference did not achieve the extension nor the conversion of implants in the platform of the abutment fitting, proposed in the present invention.

Thus, no technology was found, which is to the one presented by the invention described here for the use in prosthesis on osseointegrated implants, mainly the slanted type.

The technologies available in the state of the art have biomechanical limitations and all of them present consequences in the efficiency of the treatment, in the medium and long term.

Currently, the recommendation of slanted implants for osseointegrated rehabilitation is widespread, which minimizes the need for radical surgery, such as bone grafts. However, with the state of the art, only some angulations are corrected.

SUMMARY OF THE INVENTION

To solve such problems, the disclosed invention presents a system of prosthetic components consisting of copings and abutments that can be placed on the slanted implants with various options of angulations.

This system seeks to provide better occlusal stability and favorable biomechanics, since the masticatory loads are better distributed, diminishing the concentration of tension on the fitting platform of the implant and in the screws, due to stability rendered upon the abutment/coping, by locking with a single screw.

It is a versatile system of compensatory slanted copings, converters and extenders that function as a single coupling piece to the abutments, allowing corrections of inclinations from 0° to 60° of the osseointegrated implants, including the zygomatic fixations, and also providing properties of conversion and extension. It is a piece that adapts to the implant platform.

The whole system can be produced using a variety of materials, such as titanium, carbon, gold, chromium-cobalt, tilite, zirconium, niobium, alumina and the like, without restrictions. Furthermore, the copings, the abutments and the screws, caps and transferers of this system can receive any type of surface treatment.

The copings of the system presented herein have the property of functioning as converters, since they fit in all of the implant/abutment interfaces, even joining the different diameters of its platform and universalizing its conversion with the abutment of universal coupling to the all of the connections of the implants, whether external or internal hexagonal, internal octoganal or duodecagonal, triangular internal connection, without restrictions.

For cases of Morse cone or cold welding connection, the system of copings can provide a coupling piece or compensatory coping, converter and extender which can be adapted to the insertion axle of the implant, with a corrective plane of angulations, and can provide a fixating screw, which provides reversability to the Morse cone system.

In this system, the superior platform of the coping and the inferior base of the abutment become universalized, since the inferior platform of the coping corrects the inclination of the implant.

The capacity for extension used as transmucosal application rendered to the compensatory slanted copings, converters and extenders is carried out by means of compensation of the height of the fixations or positioning in bone and gengival of the osseointegrated implant when they are not leveled.

These characteristics of the system, in addition to allowing its use in various areas of medicine, simplify not only the selection of the abutment, but also its production on an industrial scale.

For cases of isolated or single implants, where there is a need for an anti-rotational abutment, the superior platforms of the copings and the inferior bases of the abutments can have a system of male/female type connection.

The copings of this system also have the advantage of correcting the inclinations, even before being transferred, which makes it easier and increases the possibilities of molding on the platform of the slanted implants and guarantee predictability of the final results.

The coupled planes of the compensatory copings, converters and extenders with the universal couplings abutments of this system, increase the resistance and optimize the biomechanics thereof, reducing the tension on the fixating screw of the abutment which goes through the coping and locks together the coping/abutment set.

The copings of this system can correct angulations from 0° to 60° and they can have a cylindrical or oblong shape. In the case of an oblong shape, it has a larger grooved or bezeled area, in order to adapt to the cylindrical shape of the implant.

The copings offer a fitting platform from 3.0 mm to 6.5 mm in diameter, adapting to any type of connecting fit of the implant/abutment interface, without restrictions. This fitting platform contains a hole for passing the fastening screw and locking the coping/abutment system.

The height of the compensatory slanted copings extenders, converters vary between 0.2 mm and 8.0 mm, depending on the correction of angulation, in any direction.

The thickness of the compensatory slanted copings, converters and extenders varies between 0.2 mm and 4.5 mm, and can have a straight, grooved or bezeled finishing, even on its superior and inferior platforms which, in addition to the functional, operational and aesthetic advantages, facilitates and simplifies the process of industrial production of the pieces and reduces the final cost.

This system of copings can offer a tapering at the base of the fitting of the compensatory slanted copings, converters and extenders in its whole perimeter from 0.5 mm to 1.3 mm for periodontal accommodation between the platform of the implant and the compensatory coping.

The fastening screws of this system should be larger in relation to the other screws used in the state of the art, sufficiently to compensate the height of the compensatory slanted coping, converter and extender and the locking is carried out through its head, which possesses a diameter larger than the hole in these copings.

The diameter of the fastening screw of the coping/abutment set and its hollowed area vary according to the connecting fitting of the interface of the implant itself. The diameter of the head of this screw varies between 1.3 mm and 4.0 mm, according to the fitting between the implant/coping/abutment connections.

The system of compensatory slanted copings, converters and extenders also offers the molding transferer, which has a more elongated body, with retentions and grooves to fix the impression material and it adapts to the coping through a pressure fitting along its inferior border. The system's transferer of the abutments can be fixed to the said through a longer screw.

The system of the invention also innovates in regard to the abutment of universal couplings, which can be readjusted and rounded in shape, or grooved in the superior portion, with ridges to promote greater retention in cases of cemented or screwed prostheses, for cases of multiple or isolated prostheses, which can rotational or anti-rotational This abutment has a height that varies between 3.0 mm and 8.0 mm, which can readjusted in accordance to the prosthetic-surgical planning and possesses a cylindrical body with a variable diameter between 3.5 mm and 6.5 mm.

The abutment of universal coupling can offer all of the variations of the state of the art, whether conical, mini-abutment, hexagonal, standard, trunnion, Procera® Snappy™ type abutments (by Nobel Biocare), splint, calcinable, UCLA-type, without restrictions, rotational or anti-rotational. This abutment can offer, as well, a hole in the superior portion, for the threading of the fastening screw of the prosthetic crown.

This abutment offers a hollowed area of 1.0 mm to 5.5 mm, intended to make it possible to insert the axle of the abutment screw, where the fastening screw of the abutment and the coping passes.

The internal contour of the prosthetic crown can be obtained by making a prefabricated cap or cylinder which adapts to the abutment of universal coupling, and can be made of gold, titanium, chromium-cobalt, zirconium, alumina and calcinable material, without restrictions.

This prefabricated cylinder or cap can offer a fastening screw for the screwed prostheses. In the case of cemented prostheses, only the prefabricated cylinder or cap is used, calcinable or not, and furthermore, the individualization of the abutment by means of making personalized molds.

The disclosed invention, due to its different variations of shape, height and diameter, offers better aesthetics, marginal sealing, hygienization, greater occlusal stability, as well as a reduction in treatment time and simplification of the clinical and prosthetic procedures. The advantages lead to an optimization of the surgical and rehabilitation planning.

This product, the object of the present invention, also offers clinical benefits, since it can also be used as an extender and converter.

The characteristics of this system provide great versatility, which allows its use in various medical areas.

DESCRIPTION OF DRAWINGS

The current invention can be further understood by means of FIGS. 1 to 3 presented below, where.

DETAILED DESCRIPTION OF THE FIGURES

Figure 1:
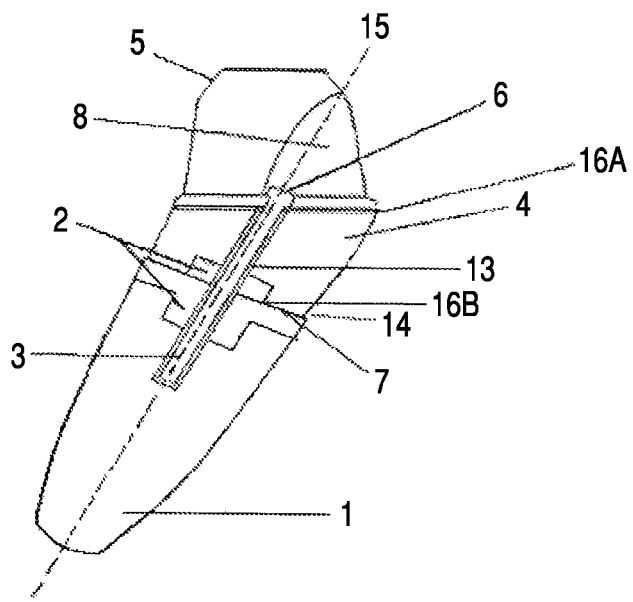
FIG. 1 shows a longitudinal cut view of the coping system in accordance with the present invention.

In the FIG. 1, the slanted implant 1 of the present invention is shown wherein a fit 2 is provided between the connections of the compensatory implant and of the coping interface, a fastening screw 3 of the abutment and of the coping being arranged in association with a compensatory slanted coping, converter and extender 4. An abutment 5 of universal coupling can be also noticed, with a head 6 of the screw 3 for locking the system. The implant 1 provides a fitting platform 7, while a hollowed area 8 is located in the abutment 5 for passing the screw 3.

According to the present invention, the compensatory slanted coping, converter and extender 4 are provided and coupled on the osteointegrated implant 1. The compensatory slanted coping, converter and extender 4, also comprises in its base (that is, the lower portion 16B) a fixed coupling piece 2 which is provided to couple the compensatory slanted coping, converter and extender 4 in the osteointegrated implant 1. To that end, the compensatory slanted coping, converter and extender 4 presents a respective connection which cooperates with said implant connection (internal or external hexagon, internal cone, Morse cone, cold welding). The compensatory slanted coping, converter and extender 4 presents a generally cylindrical or slightly oblong shape, defined by a side surface intended for periodontal accommodation between the platform of the implant and the compensatory coping, in order not to harm the bone and gum tissues, and by the upper portion 16a and lower portion 16b. As already mentioned, the planes defined by the upper portion 16a and lower portion 16b form between them an angle between 0-60 degrees, said angle defines the correction angle of the invention system. Finally, the compensatory slanted coping, converter and extender 4 also presents a through hole or a hollowed area 13 intended to allow the passage of the screw 3. This hollowed area 13 has a concentric axis with respect to insertion axle 15.

Figure 2:
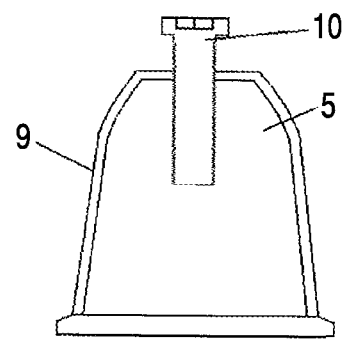
FIG. 2 shows a longitudinal cut view of the abutment of universal coupling along with the screw form prosthetic crown, in accordance with the present invention.

The longitudinal cut view of FIG. 2 illustrates the abutment of universal coupling 5 for the screwed prosthesis, wherein a cap or cylinder 9 is provided over the same and a fastening screw 10 of the prosthetic crown is treaded thereto.

Figure 3:
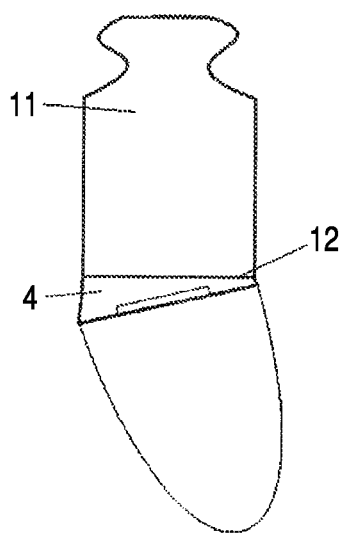
FIG. 3 shows a lateral view of the compensatory slanted coping, converter and extender, according to one embodiment of the present invention.

In the lateral view of FIG. 3 is the compensatory slanted coping, converter and extender 4 is illustrated in details, wherein the transferer 11 and the pressure fitting 12 may be observed.

Therefore, with extensive and immediate application in the area of implantodontics and other medical areas related to orthopedic and facial rehabilitation, the system presented herein justifies its protection due to its innovative character and its potential to greatly contribute to the technological development in the medical-odontological field, since the system of the invention is applicable for osseointegrated implants used in other medical areas.

REFERENCE NUMERALS USED IN THE DRAWINGS

1—Osseointegrated implant
2—Coupling piece of connections
3—Screw
4—Compensatory Slanted Coping, Converter and Extender
5—Universal Coupling Abutment
6—Head of Screw
7—Fitting Platform
8—Hollowed area
9—Cap
10—Fastening Screw
11—Transferer
12—Pressure Fitting
13—Hollowed area of screw
14—Narrowing or reduced portion of a fitting platform of coupling piece
15—Insertion axle of the implant
16A—Upper portion and universal coupling platform of Compensatory Slanted Coping Converter and Extender
16B—Lower portion and fitting platform of Compensatory Slanted Coping Converter and Extender

The invention claimed is:

1. A system of prosthetic coupled components for osseointegrated prosthetic reconstruction comprising a structure, which includes: a compensatory slanted coping, converter and extender, a universal coupling abutment; and a single screw, having a screw head, said system comprising:

said universal coupling abutment comprised of an upper frustum-conical portion and a lower frustum-conical portion, wherein the lower frustum-conical portion has a lower plane surface adapted to abut an upper portion of the coping, converter and extender, said universal coupling abutment also comprising a side hollowed area defined to permit the insertion of said single screw and said screw head positioned within the lower conical portion, to lock the compensatory slanted coping, converter and extender, the universal coupling abutment and an osseointegrated implant into the system of the prosthetic coupled components, said single screw provided to be inserted through a side hollowed area of the universal coupling abutment and a second hollowed area of the compensatory slanted coping, converter and extender and said single screw fastened inside an internally threaded hole of the osseointegrated implant, said single screw being disposed along an insertion axis of the osseointegrated implant that is coaxial with the second hollowed area of the compensatory slanted coping, converter and extender, and at an angel to an axis of the universal coupling abutment;

said compensatory slanted coping, converter and extender generally presenting one of a cylindrical or oblong shape defined by a side wall and comprising one of a through hole or the second hollowed area which is concentric and coincides in relation to an insertion axis of the implant;

wherein:

said compensatory slanted coping, converter and extender comprises a single flat upper surface and a lower surface, said single flat upper surface and said lower flat surface defining between them an angle from 0° to 60°, which defines a correction angle of the osseointegrated implant respectively between 0° to 60°;

said compensatory slanted coping, converter and extender functioning as a coupling piece formed between an interface of the osseointegrated implant and a lower plane portion of a base of the compensatory slanted coping, converter and extender and which provides a connection to the osseointegrated implant, wherein the osseointegrated implant has one of an internal or external hexagon, an internal cone, a Morse cone or a cold welding;

said compensatory slanted coping, converter and extender functioning as a universal coupling piece formed by abutting a single flat upper surface of the compensatory slanted coping, converter and extender and a lower plane surface of the universal coupling abutment, said single screw head being stopped inside of the universal coupling abutment and, after said single screw is screwed in an implant hole, said screw keeps the compensatory slanted coping, converter and extender and the universal coupling abutment firmly together with the osseointegrated implant.

2. The system of claim 1, wherein the compensatory slanted coping, converter and extender functions as a converter, which is adapted to fit one of external or internal hexagonal, internal octagonal or duodecagonal, Morse tapered or triangular internal connection type implants.

3. The system of claim 1, wherein the compensatory slanted coping, converter and extender is adapted to function as an extender to meet different heights of marginal gum in transmucosal function, obeying the gingival emergency profile.

4. The system of claim 1, wherein the compensatory slanted coping, converter and extender is adapted to be coupled to multiple osseintegrated implant connection types.

5. The system of claim 1, wherein the compensatory slanted coping, converter and extender further comprises a mold transferee with a pressure fitting.

6. The system of claim 1, wherein the compensatory slanted coping, converter and extender comprises one of a cylindrical or oblong shape, and a straight, beveled or grooved finishing end, on superior and inferior platforms.

7. The system of claim 1, wherein the compensatory slanted coping, converter and extender comprises a fitting platform for a plurality of implant connection fitting types and a corresponding hole for inserting a fastener.

8. The system of claim 7, wherein the compensatory slanted coping, converter and extender comprises a reduced portion at the fitting platform, along an entire perimeter thereof, between a platform of the implant and a platform of the compensatory slanted coping, converter and extender.

9. The system of claim 2, wherein the compensatory slanted coping, converter and extender comprises a coupling piece for use with one of Morse tapered and cold welding implants, which adapts itself to the insertion axle of the osseointegrated implant, with a corrective angular plane.

10. The system of claim 1, wherein the universal coupling abutment has one of a cylindrical shape, rounded or grooved shape, in an upper portion, and ridges for use with one of cemented, screwed, multiple or isolated, rotational or antirotational prostheses.

11. The system of claim 1, wherein, the universal coupling abutment comprises a height, which can be readjustable and additionally has a hole in an upper portion for threading the single screw having a screw head into a prosthetic crown.

12. The system of claim 1, wherein the universal coupling abutment comprises an opening for inserting the single screw having a screw head.

13. The system of claim 1, wherein the system is adapted for use with one of a conical, mini, hexagonal, standard, trunnion, splint, calcinable or UCLA type abutments.

14. The system of claim 1, wherein the single screw has a height sufficient to compensate for the height of the compensatory slanted coping, converter and extender and the screw head has a diameter between 1.3 mm to 4.0 mm, larger than the threaded hole, for locking the compensatory slanted coping, converter and extender together with the universal coupling abutment and the osseointegrated implant.

15. The system of claim 1, further comprising one of a prefabricated cap or cylinder which adapts to the universal coupling abutment, for fitting of a crown and wherein the one of a prefabricated cap or cylinder is made of one of gold, titanium, chromium-cobalt, zirconium or alumina, calcinable material.

16. The system in accordance with claim 1 wherein the universal coupling abutment can be readjusted and be one of rounded in shape or grooved in its superior portion, with ridges to promote greater retention if a prosthesis is one of cemented or screwed prostheses, for causes of multiple or isolated prosthesis which can be one of rotational or antirotational.

17. The system in according with claim 1, wherein the universal coupling abutment has a height of 3.0 to 8.0 mm.

18. The system in accordance with claim 1, wherein the compensatory slanted coping, converter and extender is connected to the osseointegrated implant by the coupling piece, and the compensatory slanted coping, converter and extender is arranged to adjust slant of the osseointegrated implant between 0° to 60°.

19. The system in accordance with claim 1, wherein a superior platform of the compensatory slanted coping, converter and extender and an inferior base of the universal coupling abutment are configured such that the coupling piece functions as a converter of multiple osseointegrated implant connections for a single universal coupling abutment.

20. The system in accordance with claim 1, wherein the implant is one of an isolated or a single implant and wherein a upper surface of the compensatory slanted coping, converter and extender and an inferior base of the universal coupling abutment are flat surfaces resulting in a system of coupled system planes type connections.

21. The system in accordance with claim 1, wherein the compensatory slanted coping, converter and extender includes a top flat surface and bottom of male/female connections.

22. The system in accordance with claim 1, wherein the universal coupling abutment possesses a cylindrical body with a variable diameter between 3.5 mm and 6.5 mm.

23. The system in accordance with claim 1, wherein the system of compensatory slanted copings, converters and extenders functions as a coupling piece to the abutments, allowing corrections of inclinations from 0° to 60° of the osseointegrated implants, and also providing properties of conversion and extension.

24. The system in accordance with claim 1, wherein the compensatory slanted coping, converter and extender is locked to the universal coupling abutment, and to the slanted implant by the single screw.

25. A dental prosthetic system, comprising:
  a coping, compensatory, converter and extender, wherein the coping, compensatory, converter and extender has a lower portion with coupling piece adapted to be coupled to an osseointegrated implant and a single flat upper surface that provides a correction of between 0° to 60° to an upper surface of the osseointegrated implant;
  a universal abutment comprised of an upper frustum-conical portion and a lower frustum-conical portion, wherein the lower frustum-conical portion has a lower surface adapted to abut an upper portion of the coping, compensatory, converter and extender, the universal abutment having parallel upper and lower surfaces adapted to abut an upper portion of the coping, compensatory, converter and extender and having the corrected angle of the osseointegrated implant, through of the lower portion of the coping, compensatory, converter and extender; and
  a single screw adapted to couple the universal abutment and the coping, compensatory, converter and extender to the osseointegrated implant;
  wherein the universal abutment comprises a first hollowed area, the coping, compensatory, converter and extender comprises a second hollowed area, and the single screw is adapted to be placed through the first hollowed area and the second hollowed area and engage a threaded inner portion of the osseointegrated implant.

* * * * *